United States Patent [19]

Buhl

[11] Patent Number: 5,488,059
[45] Date of Patent: Jan. 30, 1996

[54] TREATMENT OF ERECTILE DYSFUNCTION

[75] Inventor: Allen E. Buhl, Portage, Mich.

[73] Assignee: The Upjohn Company, Kalamazoo, Mich.

[21] Appl. No.: 250,193

[22] Filed: May 27, 1994

Related U.S. Application Data

[63] Continuation of PCT/US92/10254, Dec. 2, 1992, which is a continuation of Ser. No. 816,700, Dec. 23, 1991, abandoned.

[51] Int. Cl.$^6$ .......................... A61K 31/44; A61K 31/155
[52] U.S. Cl. ............................................. 514/349; 514/634
[58] Field of Search .................................... 514/349, 634

[56] References Cited

U.S. PATENT DOCUMENTS

| | | | |
|---|---|---|---|
| 4,057,636 | 11/1977 | Petersen | 424/263 |
| 4,127,118 | 11/1978 | Latorre | 128/79 |
| 4,521,421 | 6/1985 | Foreman | 514/267 |
| 4,801,587 | 1/1989 | Voss et al. | 514/248 |

FOREIGN PATENT DOCUMENTS 8805525  10/1988  Denmark.

OTHER PUBLICATIONS

Holmquist, et al., Effects of Pinacidil on related human *Corpus cavernosum* penis, Acta Phys Scand 138:463–469 (1990)

Giraldi, et al., Effects of Pinacidil upon penile erectile tissue, *in vitro* and *in vivo*, Pharmacology & Toxicology 67:235–238 (1990).

Holmquist, et al., $K^+$ channel openers for relaxation of isolated penile erectile tissue from rabbit, J Urol 144:146–151 (1990).

FEBS Letters, vol. 287, No. 1, 2, pp. 75–79 (Aug. 1991).

*Primary Examiner*—Zohreh Fay
*Assistant Examiner*—K. Weddington
*Attorney, Agent, or Firm*—Donald L. Corneglio

[57] ABSTRACT

A method to induce or enhance an erection or treat erectile dysfunction through the administration of a pyridylguanidine compound, preferably, N-cyano-N'(1,1-dimethyl propyl)-N" -3-pyridinyl guanidine, in low doses to the penis. Administration can be by injection into the corpus cavernosum of the penis or transdermal application.

2 Claims, No Drawings

TREATMENT OF ERECTILE DYSFUNCTION

CROSS-REFERENCE TO RELATED APPLICATIONS

This application is a continuation of International Patent Application No. PCT/US92/10254, filed Dec. 2, 1992, which is a continuation of U.S. Ser. No. 07/816,700, filed Dec. 23, 1991, abandoned.

BACKGROUND OF THE INVENTION

The present invention is directed toward the administration of a pyridylguanidine compound, preferably, N-cyano-N'(1,1-dimethyl propyl)-N"-3-pyridinyl guanidine, in low doses to the corpus cavernosum of the penis to cause or enhance an erection.

Impotency is a recognized clinical problem which affects approximately ten million men in the United States alone. This condition is due to neurological, vascular, endocrine or psychogenic pathologies that prevent an erectile response. Normally, erection involves a complex and incompletely understood mechanism by which neural stimuli induces relaxation of the penile arteries and sinusoids causing pooling of blood in the corpus cavernosum, subsequent compression of venous drainage increases the pooling of blood in the cavernosum.

Recently, the study of urology has recognized that male impotency or erectile dysfunction can be treated with medication in appropriate circumstances where the dysfunction is physiological. In such situations, an erection may be induced or enhanced by the administration of a vasodilator in the immediate vicinity of the corpus cavernosum. This treatment was reported in the U.S. Pat. No. 4,127,118 as a method for alleviating and treating male impotence by injecting into the penis an effective amount of vasodilator, a sympathomimetic amine or an andronergic blocking agent.

Since this time, numerous articles have been authored which describe the effects of vasodilators or antihypertensives to treat erectile dysfunction. Various drugs known to be useful for injection therapy are papaverine, which dilates blood vessels and is sometimes combined with phentolamine as a reinforcing effect; and prostaglandin $E_1$. A small, insulin-type syringe is used to inject the drug directly into the tissue of the penis. The basic action of the drug is to dilate blood vessels in the penis allowing them to fill with blood.

While the use of some drugs are known, the search for faster acting or more effective drugs are constantly being sought. Better drugs are sought to minimize injection dosages or avoid injection and, instead, provide a topical treatment.

INFORMATION DISCLOSURE STATEMENT

The following articles all disclose the use of pinacidil as a vasodilator in the treatment of male impotence: Holmquist, et al., Effects of Pinacidil on related human corpus cavernosum penis, Acta Phys Scand 138:463–469 (1990); Giraldi, et al., Effects of Pinacidil upon penile erectile tissue, in vitro and in vivo, Pharmacology & Toxicology 67:235–238 (1990); and Holmquist, et al., $K^+$ channel openers for relaxation of isolated penile erectile tissue from rabbit, J Urol 144:146–151 (1990).

U.S. Pat. No. 4,127,118 discloses the method of effecting or enhancing an erection by injection of a vasodilator into the penis.

U.S. Pat. No. 4,057,636 discloses the subject compounds, methods for their preparation and use as an antihypertensive.

U.S. Pat. No. 4,524,421 contains an extensive background of the erectile dysfunction art and discloses a particular quinoline for treatment of sexual dysfunction.

U.S. Pat. No. 4,801,587 discloses an ointment comprising a vasodilator, a carrier and a base for relieving impotence.

SUMMARY OF THE INVENTION

In one aspect, the present invention is a method for inducing or enhancing an erection in mammals comprising the administration of an effective amount of a compound of Formula I

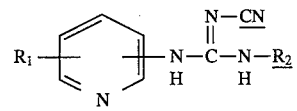

or a pharmaceutically acceptable salt thereof, wherein $R_1$ and $R_2$ are independently hydrogen, or a $C_{1-8}$alkyl, $C_{2-8}$alkenes, $C_{3-8}$cycloalkyls and isomeric forms thereof, to the penis of such mammal. Preferably, the administration is by injection into the corpus cavernosum of said penis. Alternative, the active compound can be admixed with a pharmaceutical gel and applied transdermal to the glans penis. A preferred compound of Formula I is guanidine, N-cyano-N' (1,1-dimethyl propyl)-N"-3-pyridinyl or pharmaceutically acceptable salts thereof (where $R_1$ is hydrogen and $R_2$ is 1,1-dimethyl propyl).

Where administration is by injection, the active compound is administered in an amount of from about 0.5 micrograms (μg) to about 1000 μg, preferably 5 to 10 μg.

DETAILED DESCRIPTION OF THE INVENTION

The subject invention is directed toward a treatment for impotence. Impotence is the consistent inability to achieve or sustain an erection of sufficient rigidity to have sexual intercourse. Specifically, the subject invention is a method for inducing or enhancing an erection by administering in an effective amount, preferably in low doses to the penis, a compound of Formula I:

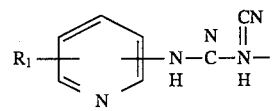

or a pharmaceutically acceptable salt thereof, wherein $R_1$ is independently hydrogen, or a $C_{1-8}$ alkyl, $C_{2-8}$ alkenes, $C_{3-8}$ cycloalkyls and isomeric forms thereof (which includes straight and branched chains). Preferably, Formula I is N-cyano-N'(1,1-dimethyl propyl)-N"-3-pyridinyl guanidine ($R_1$ is hydrogen and $R_2$ is 1,1-dimethyl propyl). Preferably, the compound is administered by injection to the penis and preferably into the corpus cavernosum of the penis. More preferably the drug can be delivered in a pharmaceutical preparation, diluent or gel, by injection or topical application, respectively.

For injection, the active compound can be diluted in a saline solution, purified water or combination thereof. Topical preparations can include the active compound with N-methyl pyrrolidone, oleyl alcohol, propylene carbonate, dimethyl sulfoxide (DMSO) or combinations thereof.

The preferred compound of the subject invention is N-cyano-N'(1,1-dimethyl propyl)-N"-3-pyridinyl guanidine although its related compounds as disclosed in U.S. Pat. No. 4,057,636 and its Reissue U.S. Pat. No. Re 31,244 (herein incorporated by reference) can be effective also.

The compound of Formula I is administered in an effective amount which is sufficient to cause or enhance the erection. Typically, the dose is from about 0.5 micrograms to about 1000 micrograms preferably from about 5 micrograms to about 10 micrograms in man. The response appears to be dose related and therefore increasing amounts are directly related to the duration or size of the erection. Of course, different male mammal species would have dosages relative to their anatomical size and weight. Calculation of dosages would be a routine calculation to anyone of ordinary skill of the art such as a veterinarian, urologist, or physician.

The pharmaceutical properties of the subject compounds to behave as a vasodilator was confirmed utilizing an in vitro rabbit mesenteric artery assay. Rabbit mesenteric artery tissue was equilibrated at one gram resting tension for one hour in physiological saline solution (PSS) prior to producing a first norepinephrine contraction. At the plateau of the first norepinephrine contraction, acetylcholine (ACH 1 µM) was added to study endothelium-dependent vasodilation. Thus, ACH-induced relaxation was routinely used as a test for the presence of functional endothelium. The tissues were washed with PSS, and were again left at the resting tension for one hour, before challenging them with the second norepinephrine contraction. At the plateau of the second norepinephrine contraction, the subject compounds were tested at concentrations of 0.01 µM to 0.5 µM. Each concentration was tested for about ten minutes or until relaxation plateaued. All compounds were not tested at all levels where vasodilation effect was or was not apparent. The percent relaxation was measured for each compound as shown in Table 1. The data was generated from 28 mesenteric rings from four rabbits.

TABLE I

| | Compound (I) | | % Relaxation | | | |
|---|---|---|---|---|---|---|
| | $R_1$ | $R_2$ | 0.01 µM | 0.05 µM | 0.1 µM | 0.5 µM |
| 1 | H | 1,1-dimethyl propyl | 81.8 | 81.0 | — | — |
| 2 | H | 1,1-dimethyl propene | 9.6 | 73.0 | — | — |
| 3 | H | 1,1-diethyl propene | 11.3 | 76.0 | — | — |
| 4* | H | 1,1-dimethyl ethylbenzene | 2.6 | 5.3 | 7.4 | 10.6 |
| 5* | H | 1,1-dimethyl methylbenzene | 0 | 6.1 | 0 | 0 |
| 6* | H | 1,1-dimethyl butyne | — | 11.2 | 6.6 | 34.6 |
| 7 | H | 1,1-dimethyl butane | 42.0 | 76.3 | — | — |
| 8 | H | 1-methyl cyclopentane | 10.5 | 81.0 | — | — |

*inactive vasodilators, not compounds of the subject invention.

Pharmaceutical evidence of a treatment to induce or effect an erection was studied using tranquilized, male cynomolgus macaque monkeys.

Intracavernous injections of test compound were given in 0.15 ml normal saline containing 0.2% DMSO. Prior to each injection, a band was placed at the base of the penis, the injection was made using a 27 gauge needle and the band removed 2 minutes later. An increase to maximal penis length, elevation off the scrotum (Rigidity), the evidence of cardiac pulse in the organ (Pulse) are good indicators of a full erection. Length was measured from the tip of the penis to a reference point marked on the abdomen near the base. Changes in length were monitored at various intervals during the trials after injection. Latency to full erection and duration of erection were recorded.

The subject compound N-cyano-N'(1,1-dimethyl propyl)-N"-3-pyridinyl guanidine, was administered to monkeys and the data collected as shown in Table II. The Pulse and Rigidity values represent the number of monkey that achieved a pulse in the penis and rigidity (penis elevated off scrotum) which are the best indicators of an erection.

TABLE II

| Concentration | Pulse | Rigidity | Time to Erection | Duration of Erection |
|---|---|---|---|---|
| 15 µg injection | 6/10 | 6/10 | 4.5 min. ± 0.7 | 18.8 ± 5.5 |
| 1.5 µg injection | 7/10 | 7/10 | 3.6 min. ± 0.5 | 14.0 ± 3.3 |
| Zero, (DMSO only) | 0/5 | 0/5 | — | — |
| 15 mg topical | 0/5 | 0/5 | — | — |

Compound N-cyano-N'(1,1-dimethyl propyl)-N"-3-pyridinyl guanidine, ("Test Compound") was compared against pinacidil to demonstrate its superior effects on inducing an erection. Both compounds were administered to monkeys and the data collected as shown in Table III. The data indicates the number of monkeys that achieved an erection per monkeys dosed at the specified concentration.

TABLE III

| Compound | Concentration | Pulse and Rigidity |
|---|---|---|
| Test* | .3 µg | 1/4 |
| | .6 µg | 2/4 |
| | 1.5 µg | 4/4 |
| Pinacidil | 1.6 µg | 0/3 |
| | 8 µg | 0/3 |
| | 16 µg | 0/3 |
| | 32 µg | 3/4 |

*N-cyano-N' (1,1-dimethyl propyl)-N"-3-pyridinyl guanidine

The test compound when compared to pinacidil was superior and showed the unexpected result of providing an erection in monkeys at significantly reduced dosage**. In fact, pinacidil at the lower dosages had no noticeable effect.

**(1.5 µg gave 4 out of 4 erections versus 32 µg of pinacidil for 3 out of 4 erections)

What is claimed:

1. A method for inducing or enhancing an erection in mammals comprising the administration of an amount of from 0.5 µg to 1000 µg of N-cyano-N'(1,1-dimethyl propyl)-N"-3-pyridinyl guanidine or a pharmaceutically acceptable salt thereof to the penis of said mammal.

2. The method of claim 1 where said compound is injected into the corpus cavernosum of a penis.

* * * * *